United States Patent [19]

Prevedello et al.

[11] 4,199,516

[45] Apr. 22, 1980

[54] 2-METHYL-2-CYANOMETHYL-5-ISOPROPYL TETRAHYDROFURAN

[75] Inventors: Aldo Prevedello; Maurizio Brunelli, both of San Donato Milanese, Italy

[73] Assignee: Anic, S.p.A., Palermo, Italy

[21] Appl. No.: 5,507

[22] Filed: Jan. 22, 1979

Related U.S. Application Data

[60] Division of Ser. No. 918,445, Jun. 23, 1978, Pat. No. 4,150,037, which is a continuation of Ser. No. 670,728, Mar. 26, 1976, abandoned.

[30] Foreign Application Priority Data

Mar. 27, 1975 [IT] Italy .............................. 21724 A/75
Nov. 27, 1975 [IT] Italy .............................. 29726 A/75

[51] Int. Cl.$^2$ ........................................... C07D 307/16
[52] U.S. Cl. ................................................ 260/346.11
[58] Field of Search ................................... 260/346.11

[56] References Cited

PUBLICATIONS

Kratochvil et al., Chemical Abstracts, vol. 75 (1971), 75958a.

*Primary Examiner*—Richard Raymond
*Attorney, Agent, or Firm*—Morgan, Finnegan, Pine, Foley & Lee

[57] ABSTRACT

In the cyclization of gamma-delta or delta-epsilon unsaturated alcohols in order to obtain certain tetrahydrofuran and tetrahydropyran derivatives which are useful in the perfuming of detergents, the improvement consisting in that the alcohol to be cyclized is reacted with a cationic ion-exchange resin. The useful temperature range is from 20° C. to 150° C: in practice the alcohol and the resin are boiled together or refluxed until the reaction is completed. A number of examples is reported and physicochemical data are given.

1 Claim, No Drawings

2-METHYL-2-CYANOMETHYL-5-ISOPROPYL TETRAHYDROFURAN

This is a division of application Ser. No. 918,445, filed June 23, 1978, now U.S. Pat. No. 4,150,037, which was a continuation of application Ser. No. 670,728, filed Mar. 26, 1976, now abandoned.

This invention relates to a method for the cyclization of gamma-delta, or delta-epsilon unsaturated alcohols and the products thus obtained.

More particularly, the present invention relates to a method for the cyclization of 3,7-dimethyl-3-hydroxy-6-octenenitrile and to the products thus obtained, namely 2,6,6-trimethyl-2-cyanomethyl-tetrahydropyran and 2-methyl-2-cyanomethyl-5-isopropyl tetrahydrofuran.

The importance is known of the tetrahydropyran and tetrahydrofuran derivatives as mainly used as perfuming agents in the formulation of detergents, on account of their considerable stability in alkaline surroundings.

A tetrahydropyran derivative is also the pink oxide, which is essential in the formulation of artificial geranium.

A number of method of synthesis of substituted tetrahydropyrans are known in the present state of the art: for example, by cyclization of glycols with removal of water, by cyclization of enolized carbonyl derivatives, by oxidizing of primary terpenic alcohols, such as citronellol. Of particular interest, due to its simple performance, is the closure of alcohols having ethylene or acetylene unsaturations, especially in an acidic medium. Several acids may be used, among which 85% formic acid, diluted sulfuric acid, a mixture of sulfuric and acetic acids, p-toluensulfonic acid, 85% phosphoric acid: a large number of these acids, however, require temperatures above room temperature. These methods are conducive to final products with poor yields.

Under this aspect, an advantage would be obtained by the method suggested by Jean Colonge and Philippe Lasfargues, as disclosed in the *Bulletin de la Société Chimique de France*, year 1962, pages 177–182. Although this method gives fair yields, it requires almost catalytic quantities of phosphoric acid (also p-toluene sulfonic acid is used in catalytic amounts, but the yields are altogether lower).

Such a method has anyhow a few drawbacks such as the difficulty of being employed for synthesizing poorly volatile derivatives, since their removal by distillation from the reaction mixture would require too high degrees of vacuum or too high temperatures, and the technical difficulty of converting such a synthesis into an industrial process which is to be carried out continuously under easily reproducible conditions. In addition to that there is also the impossibility of applying such a method to tertiary alcohols inasmuch as in such a case alkadienes would be essentially obtained.

Also for the synthesis of tetrahydrofurans several methods are known, such as by removal of water from 1,4-bihydroxyalkanes and by cyclization of olefinic alcohols, mainly beta, gamma unsaturated ones. Such methods anyhow have in general the same defects as indicated for the synthesis of tetrahydropyran derivatives.

A novel cyclization method has been found now, which employs ion-exchange resins of the cationic type which permit the cyclization of primary, secondary and also gamma-delta, or delta-epsilon tertiary unsaturated alcohols with ethylene or acetylene unsaturations without having such a cyclization accompanied by dehydration, a fact which is absolutely surprising, inasmuch as it is known in the art that such resins catalyze the dehydration of such alcohols, especially the tertiary ones. Such a cyclization, according to the method of the present invention, takes place, moreover, with best yields, as it is conducive to the formation of pyran or furan derivatives or an admixture thereof with a satisfactory conversion and selectivity. Under these conditions, in point of fact, virtually no side reactions are experienced, such as the elimination of water and the formation of pitches or resinous products. In addition, further advantages are obtained since it is possible to operate by diluting the alcohol in an inert solvent, the latter being capable of being easily removed on completion of the reaction, while dispensing with intricate dilution, neutralization and extraction procedures, which are conversely necessary whenever acids in solution are used. Such a cyclization reaction, as catalyzed by cation ion-exchange resins, can easily be converted, with conventional techniques, into a continuous industrial production run.

Such a cyclization method is carried out by diluting the alcohol to be cyclized in an inert solvent and then contacting such a solution with a cationic-type ion-exchange resin.

Various types of cationic exchange resins can be used, the quantity of them to be used being a function of the milliequivalent contents of acidic groups per gram of resin.

At any rate, in the ensuing description, reference will be had to the resin of the type Amberlyst 15 (H) (a coarse-lattice cationic resin produced by Rohm and Haas Co., Philadelphia and containing about 4.6 milliequivalents of sulfonic groups per gram of resin) and the percentages as reported herein are intended to be referred to this resin.

Such a process can take place, in addition, with a high selectivity, within a wide temperature range, more particularly between 20° C. and 180° C., it being also possible to adopt higher temperatures but consistently with the stability of the resin concerned. It has been found that it is possible to direct the cyclization of the gamma-delta or delta-epsilon unsaturated alcohols towards the formation of either the tetrahydropyran or the tetrahydrofuran derivative or a mixture of them, as a function of the amount of resin used, or, more exactly, of the ratio of the cationic-type ion-exchange resin to the unsaturated alcohol and/or of temperature.

As a matter of fact, for temperatures lying in the range 20° C.–150° C., preferably between 80° C. and 120° C., and in the presence of almost catalytic amounts of a sulfonic resin, the reaction is directed towards the formation of tetrahydropyran derivative, whereas by employing a quantity of the cationic-type ion-exchange resin which exceeds the catalytic amount until attaining weight ratios of the resin to the alcohol of 1 or higher, the reaction is directed towards the formation of the tetrahydrofuran derivative. It has been likewise found that the increase of the temperature, alone, still in the presence of almost catalytic amounts of resin, encourages the formation of the tetrahydrofuran derivative. The concurrent action of these two parameters enhances the formation of the tetrahydrofuran derivative, so that, the conversion ratings being equal, it is possible to use amounts of the resin which are smaller than those to be used when these two parameters are caused to act separately.

The simultaneous increase of these two parameters thus permits to obtain, when the conversion ratings are the same, reaction times which are positively shorter than those to be used when a single parameter is increased.

This reaction for the formation of the tetrahydrofuran derivative can be appropriately carried out at temperatures in the range between 80° C. and 180° C. or above, consistently with the stability of the resin and/or in the presence of an amount of ion-exchange resin which is varied from almost catalytic amounts to attaining ratios of the resin to the alcohol, by weight, which are equal to one or are even higher.

In the case that two of these variables are caused to act simultaneously, it is preferred that the temperature may lie between 120° C. and 150° C. and the ratio of the resin to the alcohol, by weight, is in the neighborhood of one.

If the temperature is the only variable which directs the reaction towards the formation of the tetrahydrofuran derivative, it can be varied, preferably, between 150° C. and 180° C. or above, consistently with the stability of the resin.

Thus, in the case where the amount of resin is the only factor to direct the reaction towards the obtention of the tetrahydrofuran derivative, the ratio of the amount of resin to the weight of the alcohol will preferably selected at about one or higher.

Intermediate variations of either variable, in the case in which they act individually, or decreases of the reaction time, when the two variables act concurrently, are conducive to the formation of mixtures having various compositions, of the tetrahydrofuran and the tetrahydropyran derivatives, said mixtures being susceptible, in a few cases, of being used directly as such.

Moreover, it has been surprisingly found that the tetrahydrofuran derivatives the subject of the present invention can be obtained, as an alternative, by rearrangement of the tetrahydropyran derivatives by adopting reaction conditions (quantity of the resin and/or temperature) akin to those used for obtaining the tetrahydrofuran derivatives starting from their corresponding unsaturated alcohols.

As outlined above, it has now been found that the cyclization reaction of the 3,7-dimethyl-3-hydroxy-6-octenenitrile can be directed towards the obtention of the tetrahydrofuran derivative by employing a quantity of ion-exchange resin of the cationic type which is larger than the catalytic amount until attaining weight ratios of the resin to the alcohol which are equal to one or higher than that.

It has been likewise found that even the temperature increase alone, still in the presence of almost catalytic amounts of the resin, encourages the formation of the tetrahydrofuran derivative.

The coacting influence of these two factors enchances the formation reaction of the tetrahydrofuran derivatives so that, the conversion rating being the same, it is possible to use both temperature conditions and resin amounts which are less drastic as compared with those to be used when these two variables are caused to act separately and individually.

Quite particular an example of cyclization according to the method of this invention is the synthesis of the compound 2,6,6-trimethyl-2-cyanomethyl-tetrahydropyran, which is an additional subject-matter of the present invention and has the followin structural formula:

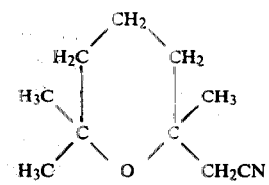

Such a compound, in addition to possessing very pleasing odoriferous properties as well as a good stability to alkalies, has a nitrile group which can be converted, according to known methods, into an ester, an amide, an amine, an aldehyde and other compounds. Such a novel compound is synthetized by cyclization of the 3,7-dimethyl-3-hydroxy-6-octenenitrile. The reaction can be carried out with advantage by diluting 3,7-dimethyl-3-hydroxy-6-octenenitrile with toluene and keeping the admixture to its boiling point (111° C. approx.) in the presence of catalytic amounts of a sulfonic resin.

An additional example of cyclization is the synthesis, with good yields and selectivity, of a novel compound, the 2-methyl-2-cyanomethyl-5-isopropyl-tetrahydrofuran, while still using 3,7-dimethyl-3-hydroxy-6-octenenitrile as the starting compound and in the presence of a cationic resin, but appropriately changing the ratio of the exchange resin to the unsaturated alcohol and/or the temperature.

Such a novel compound can also be obtained, as already outlined above, in the most general use, by rearranging the 2,6,6-trimethyl-2-cyanomethyl tetrahydropyran under conditions similar to those used for the obtention of 2-methyl-2-cyanomethyl-5-isopropyl tetrahydrofuran starting from 3,7-dimethyl-3-hydroxy-6-octenenitrile.

For a better understanding of the present invention, a few Examples are given, which are illustrations and not limitations of the present invention. Examples 1 and 2 are comparative and are reported herein to make the advantages of the method of this invention fully conspicuous.

EXAMPLE 1

Forty (40) grams of 3,7-dimethyl-3-hydroxy-6-octenenitrile are charged during 5 minutes in a 2-liter flask which is magnetically stirred and contains 400 mls. of 85% phosphoric acid. The solution is maintained vigorously stirred during 15 minutes whereafter there are poured in the flask, which is immersed in a cold water bath, 600 mls. of deionized water. Extraction with ethyl ether is then carried out, the ethereal extracts are combined, washed once with water and then with a saturated sodium bicarbonate solution and then with water until neutrality is reached. The ethereal extracts are dried over sodium sulphate overnight, then filtration is carried out and the solvent distilled off. There are obtained 39.3 grams of a raw product on which the yields are determined by means of gaschromatography in the presence of an internal standard:

Conversion: 98%, selectivity: 68%, Yield: 66%

The tetrahydropyran derivative can be obtained in a pure state by fractionation: its boiling point is 80° C.–81° C. under 3 millimeters of mercury, abs.pressure. The principal spectroscopical specifications of the 2,6,6-trimethyl-2-cyanomethyl tetrahydropyran are:

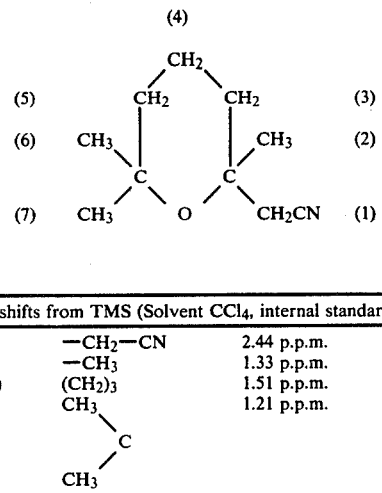

| Chemial shifts from TMS (Solvent CCl₄, internal standard HMDS) | | | |
|---|---|---|---|
| (1) | —CH$_2$—CN | 2.44 p.p.m. | S |
| (2) | —CH$_3$ | 1.33 p.p.m. | S |
| (3,4,5) | (CH$_2$)$_3$ | 1.51 p.p.m. | m |
| (6,7) | CH$_3$\C/CH$_3$ | 1.21 p.p.m. | S |

I.R: 2980 st, 2940 st, 2240 m, 1470 m, 1455 m, 1420 w, 1375 st, 1365 m, 1355 m, 1225 st, 1215 m, 1120 st, 1100 w, 1080 w, 1070 st, 1030 st, 1000 st, 990 st, 830 m, 815 w, 705 w, 695 w.

M.S.: The mass spectrum does not exhibit molecular ion; it shows significant ions at m/e 152 (C$_9$H$_4$NO)$^+$ and at m/e 127 (C$_8$H$_{15}$O)$^+$ the formulas having been ascertained for both high resolution, the ions being characteristic of a fragmentation of the kind:

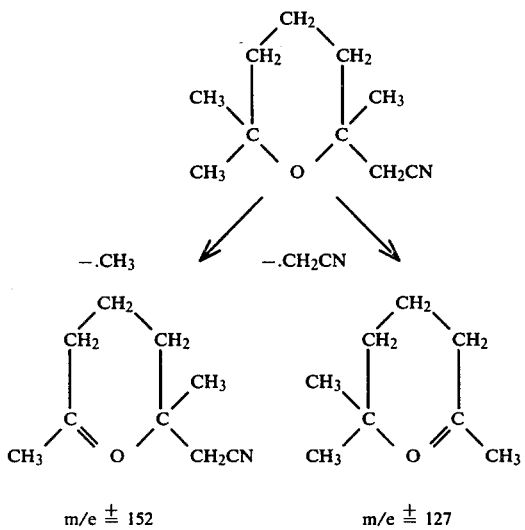

Elemental analysis:

| | Calculated | Found |
|---|---|---|
| C% | 71.9 | 71.9 |
| H% | 10.2 | 10.5 |
| N% | 8.4 | 8.7 |

EXAMPLE 2

A 500-ml flask, externally cooled with ice and having a stirrer with a glass paddle is charged with 100 grams of 85% phosphoric acid to which there are added, with stirring and dropwise, 10 grams of 3,7-dimethyl-3-hydroxy-6-octenenitrile. On completion of the addition the flask, which is also fitted with a bulb condenser, is immersed in a thermostatic bath set at 80° C. and, still with stirring, the reaction is allowed to go on during 5 hours. Then, upon cooling, the mixture is poured in a beaker containing 300 grams of ice. An oil is formed which sticks to the vessel walls: it is repeatedly washed with a saturated solution of sodium bicarbonate and then with water to neutrality. The oil is dried in vacuum, washed with a small amount of ethyl ether and then dried in a vacuo again.

A very viscous pitch is obtained which cannot be distilled, even under a very high vacuum and at high temperatures.

EXAMPLE 3

40 (forty) grams of 3,7-dimethyl-3-hydroxy-6-octenenitrile are charged in a 1000-ml flask equipped with a mechanical stirrer and a bubble condenser: there are subsequently added 400 mls toluene and 8 grams of Amberlyst 15 (H) (a coarse-lattice cationic resin produced by Rohm and Haas Co. of Philadelphia and formed by a styrenedivinylbenzene copolymer which contains 4.6 milliequivalent of sulfonic groups per gram of resin). The mixture is kept boiling and vigorously stirred during 3 hours. Upon cooling the resin is filtered off, washed with toluene and the solvent is then evaporated off.

On the raw reaction product, the conversion rating, the yield and the selectivity are determined as disclosed in Example 1:
Conversion: 98%
Selectivity: 92%
Yield: 90%

Both gaschromatography and mass spectrometry confirm that the same tetrahydropyran derivative as obtained in Example 1 is in the question.

EXAMPLE 4

10 grams of 3,7-dimethyl-3-hydroxy-6-octenenitrile are charged in a 500-ml flask equipped with a mechanical stirrer and a bulb condenser. 100 mls of tetrahydrofuran are then charged and there are added 2 grams of Amberlyst 15 (H) (see EXAMPLE 3). Boiling and vigorous stirring are maintained during 25 hours. Upon cooling, the resin is filtered off, washed with tetrahydrofuran and the solvent is then stripped. On the raw material, the conversion rating, the yield and the selectivity are determined, as related to the tetrahydropyran derivative:
Conversion: 88%
Selectivity: 83%
Yield: 73%

EXAMPLE 5

10 grams of 3,7-dimethyl-3-hydroxy-6-octenenitrile are diluted with about 100 mls dioxane (b.p. 100° C.–102° C.) and charged in a flask equipped with a mechanical stirrer and a bubble condenser. Then, 2 grams of Amberlyst 15 (H) (see EXAMPLE 3) are added. The mixture is brought to a boil and stirring is continued vigorously during 3 hours, then the mixture is allowed to cool, the resin is collected on a filter and washed with dioxane, the solvent being then distilled off:
Conversion: 91%
Selectivity: 87%

Yield: 79%

EXAMPLE 6

70 grams of 3,7-dimethyl-3-hydroxy-6-octenenitrile (98% purity) are charged in a 2-liter flask equipped with a mechanical stirrer, a bubble condenser, a thermometer and a screwed-in plug having a silicone diaphragm to effect occasional samplings.

Subsequently, 700 mls of toluene and 70 grams of Amberlyst 15 (H) (coarse-lattice cationic resin produced by Rohm & Haas Co. of Philadelphia and composed by a styrene-divinylbenzene copolymer containing about 4.6 milliequivalents of sulfonic groups per gram of resin) are added.

The mixture is refluxed while maintaining it stirred during 14 hours. Then the mixture is allowed to cool, filtered and the resin is washed with toluene and the solvent is distilled off.

There are obtained 75 grams of a raw product (it still contains some toluene) on which conversion, yield and selectivity are determined in terms of tetrahydrofuran derivative by means of gaschromatography in the presence of an internal standard.

Conversion: 99%

Selectivity and yield: 70% for both

It should be noted that, by stopping the reaction within a shorter time, mixtures of various compositions of tetrahydrofuran and tetrahydropyran derivatives are obtained.

A sample of 2-methyl-2-cyanomethyl-5-isopropyl tetrahydrofuran, purified by fractional distillation, has been tested with I.R., N.M.R. and M.S. and gaschromatographically analysed on a capillary column. The results are as follows:

(a) Gaschromatography on capillary column

A gaschromatographical analysis on a 150'×0.02" Carbowax 20M capillary column has been carried out at a constant temperature of 150° C.

Two main retention peaks have been detected, of 54 min 45 sec and 56 min 10 sec.

The peaks have roughly the same area (the first peak is approximately 46% of the sum of the two).

(b) Mass Spectrometry

The mass spectrum exhibits a molecular ion of weak intensity, $-M^+$ (1%) at 167 m/e.

Significant fragments are present, which correspond to the loss of several substituents on the carbon atoms in the alpha position to oxygen, with the formation of stable oxonium ions.

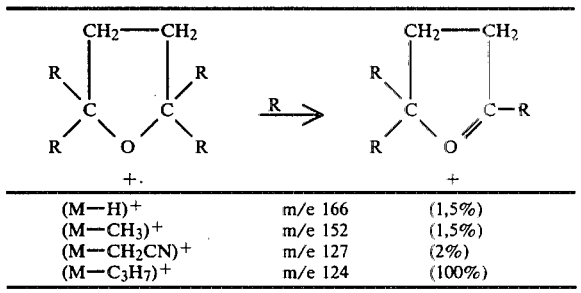

| | | |
|---|---|---|
| $(M-H)^+$ | m/e 166 | (1,5%) |
| $(M-CH_3)^+$ | m/e 152 | (1,5%) |
| $(M-CH_2CN)^+$ | m/e 127 | (2%) |
| $(M-C_3H_7)^+$ | m/e 124 | (100%) |

(c) N. M. R.

The $^1$HN.M.R. spectrum clearly shows the presence of the cis- and trans- isomers of 2-methyl-2-cyanomethyl-5-isopropyl tetrahydrofuran in nearly equimolecular quantities.

The values of the chemical shifts are reported below without specifying their allotments to the individual isomers:

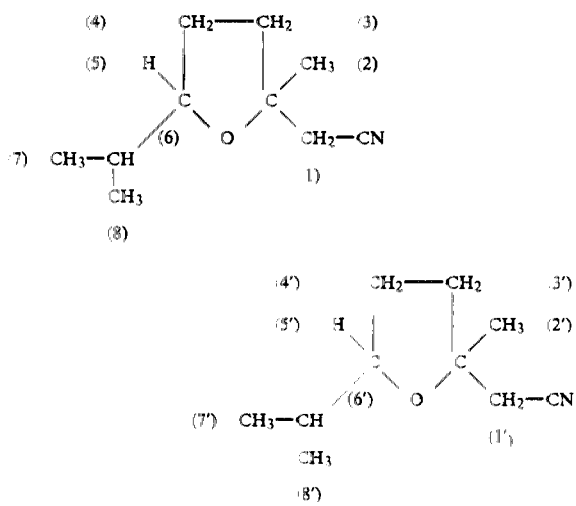

| Chemical Shifts from TMS (solvent CDCl₃ - internal standard TMS) | | | | |
|---|---|---|---|---|
| 5-5' | \C/H \O/ | 3.70 | p.p.m. | m |
| 1-1' | —CH₂—CN | 2.52 | p.p.m. | s |
| | | 2.50 | p.p.m. | s |
| 4-3:4'-3' | (CH₂)₂ | 2.18-1.50 | p.p.m. | m |
| | | 2.18-1.50 | p.p.m. | m |
| 6-6' | \CH— / | 2.18-1.50 | p.p.m. | m |
| 2-2' | \C/CH₃ | 1.33 | p.p.m. | s |
| | | 1.32 | p.p.m. | s |
| 8-8 7'-8' | CH₃\ /C/ \CH₃ | 0.94 (J = 7 Hz) | p.p.m. | d |
| | | 0.86 (J = 7 Hz) | p.p.m. | d |

| a) I. R. (in cm⁻¹) | | | |
|---|---|---|---|
| 2980 st | 2960 st | 2940 st | 2250 m |
| 1565 m | 1470 st | 1460 m | 1420 w |
| 1380 st | 1320 w | 1280 w | 1260 vw |
| 1230 w | 1180 vw | 1115 st | 1080 vw |
| 1045 st | 1010 vw | 975 vw | 920 w |
| 850 m | 830 vw | 770 w | 705 vw |
| 650 w | | | |

EXAMPLE 7

30 grams of 3,7-dimethyl-3-hydroxy-6-octenenitrile are charged in a 500-ml flask equipped with a mechanical stirrer and a bubble condenser.

There are charged 300 mls of xylene along with 40 grams of Amberlyst 15 (H) resin ( a coarse-lattice cationic resin produced by Rohm & Haas Co. of Philadelphia and composed by a styrenedivinylbenzene copolymer containing about 4.6 milliequivalents of sulfonic groups per gram of resin).

The mixture is brought to a boil (temperature 136° C.-138° C.) and stirring is maintained during 3 hours. The mixture is then cooled, filtered and washed with xylene.

The resins are then extracted in a Kumagawa extractor with xylene during about 10 hours. The xylene solutions are combined and, on them, conversion, selectivity and tetrahydrofuran derivative yields are determined by means of gaschromatography in the presence of an internal standard:
  Conversion: 99%
  Yield: 68%
  Selectivity: 69%

EXAMPLE 8

30 grams of 2,6,6-trimethyl-2-cyanomethyl tetrahydropyran (95.5% purity) containing 3.3% of 2-methyl-2-cyanomethyl-5-isopropyl tetrahydrofuran are poured in a 1000-ml flask equipped with a mechanical stirrer and bubble condenser.

There are subsequently added 300 mls xylene and 40 grams of Amberlyst 15 (H) resin (a coarse-lattice cationic resin produced by Rohm & Haas Co. Philadelphia and composed by a styrenedivinylbenzene copolymer containing about 4.6 milliequivalents of sulfonic groups per gram of resin).

The mixture is refluxed (136° C.-138° C.) and kept stirred during 2 hours. Then it is allowed to cool, filtered and the resin is washed with xylene.

In addition, the resins are extracted in a Kumagawa extractor with xylene during 10 hours. The two solutions are combined and on these the yield, the conversion and the selectivity are determined, referred to the tetrahydrofuran derivative, by gaschromatography in the presence of an internal standard:
  Conversion: 91.4%
  Selectivity: 77.4%
  Yield: 70.9%

EXAMPLE 9

20 grams of 3,7-dimethyl-3-hydroxy-6-octenenitrile (purity 98%) are charged in a 500-ml flask equipped with a mechanical stirrer and a bubble condenser.

200 mls of xylene and 4 grams of Amberlyst 15 (H) resin are then charged (a coarse-lattice cationic resin produced by Rohm & Haas Co. Philadelphia and composed by a styrene-divinylbenzene copolymer containing about 4.6 milliequivalents of sulfonic groups per gram of resin).

The mixture is brought to a boil (136° C.-138° C.) and kept stirred during 14 hours, then is allowed to cool, filtered and washed with xylene.

By means of gaschromatography in the presence of an internal standard the yields in tetrahydrofuran derivative and tetrahydropyran derivatives are determined.
  Conversion: 99%
  Tetrahydropyran derivative yield: 34%
  Tetrahydrofuran derivative yield: 42%

EXAMPLE 10

30 grams of 3,7-dimethyl-3-hydroxy-6-octenenitrile (purity 98%) are charged in a 500-ml flask equipped with a mechanical stirrer and a bubble condenser.

There are loaded, then, 4 grams of Amberlyst 15 (H) resin (a coarse-lattice cationic resin produced by Rohm & Haas Co., Philadelphia and composed by a styrenedivinylbenzene copolymer containing about 4.6 milliequivalents of sulfonic groups per gram of resin) and 200 mls of tetrahydronaphthalene.

The flask is placed in a thermostat and the mixture is kept stirred at 180° C.

The chromatographic analysis carried out in different times shows a gradual increase in the ratio of the area of the tetrahydrofuran derivative to the sum of the areas of the tetrahydrofuran and the tetrahydropyran derivatives.

After 9½ hours the reaction mixture is cooled, filtered and the resin is washed. On the reaction raw product there are determined the conversion rating and the yields in tetrahydrofuran and tetrahydropyran derivatives by means of gaschromatography in the presence of an internal standard:
  Conversion: 99%
  Tetrahydrofuran derivative yield: 34%
  Tetrahydropyran derivative yield: 9%

What we claim is:

1. As a new composition of matter, 2-methyl-2-cyanomethyl-5-isopropyl tetrahydrofuran having the following structural formula:

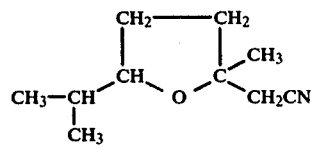

* * * * *